(12) United States Patent
Kim et al.

(10) Patent No.: US 9,700,630 B2
(45) Date of Patent: Jul. 11, 2017

(54) LOW MOLECULAR WEIGHT METHYL CELLULOSE-BASED PARENTERAL DRUG DELIVERY SYSTEM

(71) Applicant: INDUSTRY-UNIVERSITY COOPERATION FOUNDATION HANYANG UNIVERSITY, Seoul (KR)

(72) Inventors: Yong-Hee Kim, Seoul (KR); Jang Kyoung Kim, Seoul (KR)

(73) Assignee: INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 0 days.

(21) Appl. No.: 14/890,330

(22) PCT Filed: May 9, 2014

(86) PCT No.: PCT/KR2014/004120
§ 371 (c)(1),
(2) Date: Nov. 10, 2015

(87) PCT Pub. No.: WO2014/182101
PCT Pub. Date: Nov. 13, 2014

(65) Prior Publication Data
US 2016/0106848 A1 Apr. 21, 2016

(30) Foreign Application Priority Data
May 10, 2013 (KR) .................. 10-2013-0053165

(51) Int. Cl.
*A61K 47/38* (2006.01)
*A61K 9/06* (2006.01)
*A61K 9/00* (2006.01)
*A61K 38/18* (2006.01)
*A61K 38/22* (2006.01)
*A61K 38/38* (2006.01)
*C12P 19/04* (2006.01)
*C12P 19/14* (2006.01)
*A61K 38/26* (2006.01)

(52) U.S. Cl.
CPC ............ *A61K 47/38* (2013.01); *A61K 9/0024* (2013.01); *A61K 9/06* (2013.01); *A61K 38/1825* (2013.01); *A61K 38/22* (2013.01); *A61K 38/26* (2013.01); *A61K 38/385* (2013.01); *C12P 19/04* (2013.01); *C12P 19/14* (2013.01); *A61K 9/0019* (2013.01)

(58) Field of Classification Search
CPC .... A61K 38/1825; A61K 38/22; A61K 38/26; A61K 38/385; A61K 47/38; A61K 9/0019; A61K 9/0024; A61K 9/06; C12P 19/04; C12P 19/14
See application file for complete search history.

(56) References Cited

U.S. PATENT DOCUMENTS 3,856,941 A * 12/1974 Turner .................. A61K 8/042
424/617

FOREIGN PATENT DOCUMENTS

| KR | 10-0813224 B1 | 3/2008 |
| KR | 10-2010-0097075 A | 9/2010 |
| KR | 20100097075 | 9/2010 |

OTHER PUBLICATIONS

Kunihiko et al, (Pharmaceutical and Chemical Bulletin, 2010, vol. 58, pp. 247-249).*
Sandeep Kumar, et al., "In Situ-Forming Gels for Ophthalmic Drug Delivery", Journal of Ocular Pharmacology, vol. 10, No. 1, Total 13 Pages, (1994).
Kunihiko Itoh, et al., "Effect of $_D$-Sorbitol on the Thermal Gelation of Methylcellulose Formulations for Drug Delivery", Chemical and Pharmacueutical Bulletin, vol. 58, No. 2, pp. 247-249, (2010).
Manas Bhowmik, et al., "Effect of salts on gelation and drug release profiles of methylcellulose-based ophthalmic thermos-reversible in situ gels", Pharmaceutical Development and Technology, vol. 16, No. 4, pp. 385-391, (2011).
International Search Report Issued Aug. 27, 2014 in PCT/KR14/004120 Filed May 9, 2014.
Y. Xu, et al., "Salt-Assisted and Salt-Suppressed Sol-Gel Transitions of Methylcellulose in Water", Langmuir, 2004, 20, 646-652.

* cited by examiner

*Primary Examiner* — Mark V Stevens
(74) *Attorney, Agent, or Firm* — Oblon, McClelland, Maier & Neustadt, L.L.P.

(57) ABSTRACT

The present invention relates to a parenteral drug delivery carrier and a drug delivery system that use a thermosensitive gel based on methyl cellulose alone as a low molecular weight polysaccharide without a salting-out salt. The single use of the low molecular weight methyl cellulose as a natural polymer increases the biocompatibility and biodegradability of the drug delivery system. Therefore, the drug delivery system is suitable for use in the preparation of a sustained release composition for parenteral drug delivery.

9 Claims, 7 Drawing Sheets

LOW MOLECULAR WEIGHT METHYL CELLULOSE-BASED PARENTERAL DRUG DELIVERY SYSTEM

TECHNICAL FIELD

The present invention relates to a parenteral drug delivery system. More specifically, the present invention relates to a parenteral drug delivery system using a thermosensitive gel based on methyl cellulose alone as a low molecular weight polysaccharide without a salting-out salt.

BACKGROUND ART

In situ forming systems have been reported in the literature for various biomedical applications, including drug delivery and tissue culture treatment, over the past few years (see R. L. Dunn et al., Biodegradable in-situ forming implants and methods of producing the same, US Patent 4 (1990) 938-763; B. O. Haglund et al., J. Control. Release 41 (1996) 29-235; and Y. An et al., J. Control. Release 64 (2000) 205-215).

There are several possible mechanisms that lead to in situ gel formation: solvent exchange, pH change, ultraviolet (UV) irradiation, ionic cross-linkage, and temperature modulation. Negative thermosensitive polymers having a lower critical solution temperature (LCST)) and thermoreversible hydrogels undergoing a reversible sol-gel transition upon heating or cooling are the most commonly investigated materials in stimuli-sensitive polymer systems for drug delivery.

Some synthetic polymers were reported to exhibit thermoreversible gelation behavior at body temperature and were used for drug delivery, but their inherent problems associated with biocompatibility and biodegradability still remain unsolved.

In this connection, Korean Patent No. 10-0813224 issued to the present inventors discloses a protein drug delivery system based on high molecular weight methyl cellulose as a natural polymer and coacervates.

Many technologies for drug delivery are known. Such technologies are, for example, drug delivery technologies using polymers, drug delivery technologies using protein drugs, drug delivery systems using PLGA-PEG-PLGA-based synthetic polymers, and drug delivery systems using gel depots.

However, these technologies suffer from several problems, including insufficient biocompatibility of the synthetic polymers, residual toxic chemicals, and complicated processes. Other challenges related to the synthetic polymers have higher gelling temperatures compared to body temperature and reduced elimination efficiency due to their high molecular weights, and the time-controlled release of drugs is difficult to obtain. Furthermore, the synthetic polymers tend to lose their gel shape by dilution in the presence of excessive body fluids. The addition of toxic salting-out salts may cause poor biocompatibility.

Thus, there is an urgent need to develop a new drug delivery system that is free from associated with biocompatibility and biodegradability of polymers, increases the stability of a drug, enables a single dosage of a drug intended for long-term administration, and is injected into a tissue around a target to deliver a drug to the target with high efficiency.

As a result of repeated research, the present inventors have found that gelation of low molecular weight methyl cellulose alone as a natural polymer without a salting-out salt at body temperature enables the production of an effective thermosensitive gel for parenteral drug delivery. The present invention has been achieved based on this finding.

DETAILED DESCRIPTION OF THE INVENTION

Problems to be Solved by the Invention

One object of the present invention is to provide a highly biocompatible and biodegradable thermosensitive gel for parenteral drug delivery and a method for producing the same.

A further object of the present invention is to provide a sustained release composition for parenteral drug delivery that slowly releases a drug in vivo when injected into a target site in the body.

Means for Solving the Problems

One aspect of the present invention provides a thermosensitive gel for parenteral drug delivery composed of methyl cellulose having a molecular weight of 10 to 20 kDa without a salting-out salt.

A further aspect of the present invention provides a sustained release composition for parenteral drug delivery including the thermosensitive gel and a hydrophilic drug, a protein drug or a nucleic acid-based drug.

The thermoreversible methyl cellulose having a molecular weight of 10 to 20 kDa preferably has an average molecular weight of 15 kDa and is converted to a gel at a body temperature in the range of 35 to 40° C.

For example, the thermoreversible methyl cellulose within the molecular weight range of 10 to 20 kDa may be prepared by treating methyl cellulose of molecular weight 50 to 70 kDa with cellulase and dialyzing the enzymatically treated methyl cellulose using a dialysis membrane.

The thermosensitive gel of the present invention may deliver any drug, preferably a hydrophilic drug, a protein drug or a nucleic acid-based drug. The amount of the drug may be from 0.1% to 100% by weight with respect to the amount of the thermosensitive gel.

Another aspect of the present invention provides a sustained release composition for parenteral drug delivery including the thermosensitive gel and a hydrophilic drug.

That is, the composition of the present invention is administered parenterally. The term "parenteral" means intramuscular, intraperitoneal, intraabdominal, subcutaneous, intravenous or intraarterial.

Accordingly, the sustained release composition for parenteral drug delivery according to the present invention is preferably formulated into a typical injectable preparation.

The thermosensitive gel of the present invention, together with a drug, can be easily injected into the body through a syringe. The injected thermosensitive gel is converted to a hard gel state at body temperature and thereafter slowly releases the drug. Therefore, the thermosensitive gel of the present invention increases the stability of a drug, enables a single dosage of a drug intended for long-term administration, and can be injected into a tissue around a target to deliver a drug to the target with high efficiency.

Effects of the Invention

The parenteral drug delivery system of the present invention is based on low molecular weight methyl cellulose alone as a natural polymer and is thus free from toxicity problems encountered in the use of salting-out salts in conventional parenteral drug delivery systems, ensuring high biocompatibility and biodegradability.

Particularly, the low molecular weight methyl cellulose is gelled at body temperature to slowly release a drug in vivo and it per se is slowly degraded in vivo into lower molecular weight substances harmless to humans, which are then released in vivo. Therefore, there is no need for a separate surgical operation to remove the gel after release of the drug over a predetermined time period. In addition, since a single dosage of the parenteral drug delivery system is sufficient to maintain the pharmacological effects of the drug, the need for frequent administration of the parenteral drug delivery system can be avoided, ensuring improved convenience for patients. The formed gel is maintained for a long period of time and thus exhibits many outstanding effects, such as release of the drug over a desired period of time. Therefore, the gel is very useful as a drug delivery carrier.

BEST MODE FOR CARRYING OUT THE INVENTION

The definitions of the terms used herein are as follows.

"Sol" means a dispersion of colloidal particles within a liquid. The term "gel" means a strong network in which polymer chains whose average length is typically greater than 1 micrometer are interconnected with pores having dimensions of 1 micrometer or less (submicrometer) and refers to a semisolid phase that spontaneously occurs as the temperature of a polymer solution is raised to or above the gelation temperature of a block copolymer.

"Gelation temperature" means the temperature at which a biodegradable block copolymer undergoes reverse thermal gelation, i.e. the temperature below which the block copolymer is soluble in water and above which the block copolymer undergoes a phase transition, resulting in an increase in viscosity or the formation of a semisolid gel. "Gelation temperature" has the same meaning as "reverse thermal gelation temperature."

"Reverse (negative) thermal gelation" is the phenomenon in which a solution of a block copolymer spontaneously increases in viscosity or transforms into a semisolid gel as the temperature of the solution is increased above the gelation temperature of the copolymer. "Gel" includes both the semisolid gel state and the high viscosity state that exists above the gelation temperature. When cooled below the gelation temperature, the gel spontaneously reverses to reform the lower viscosity solution. This cycling between the solution and the gel may be repeated indefinitely because the sol/gel transition does not involve any change in the chemical composition of the polymer system. All interactions to create the gel are physical in nature and do not involve the formation or breaking of covalent bonds.

"Biodegradable" means that block copolymer components can chemically break down or degrade within the body to form nontoxic components.

"Biocompatible" means that a material interacts with the body without undesirable aftereffects.

"Sustained release" refers to the continual release of a drug or therapeutic agent or any combination thereof over a period of time.

"Controlled release" refers to control of the rate and/or quantity of a drug or therapeutic agent delivered according to drug delivery formulations of the invention. The controlled release can be continuous or discontinuous, and/or linear or non-linear. This can be accomplished using one or more types of polymer compositions, drug loadings, inclusion of excipients or degradation enhancers, or other modifiers, administered alone, in combination or sequentially to produce the desired effect.

"Drug" shall mean any organic or inorganic compound or substance having bioactivity and used or adapted for therapeutic purposes. Proteins, oligonucleotides, DNA, and gene therapy agents are broadly covered by the definition of the drug.

"Therapeutic agent" refers to any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like.

"Peptide," "polypeptide," "oligopeptide," and "protein' when referring to a peptide or protein drugs will be used interchangeably and will be limited to any particular molecular weight, peptide sequence or length, biological activity or therapeutic application areas.

"Therapeutic effect" means any improvement in the condition of a subject, human or animal, treated according to the subject method, including obtaining a preventative or prophylactic effect, or any alleviation of the severity of signs and symptoms of a disease, disorder, or condition which can be detected by means of physical examination, laboratory or instrumental methods.

As used herein, unless otherwise defined in conjunction with specific diseases or disorders, the term "treat" or "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

As used herein, the terms "about", "substantially", etc. are intended to allow some leeway in mathematical exactness to account for tolerances that are acceptable in the trade and to prevent any unconscientious violator from unduly taking advantage of the disclosure in which exact or absolute numerical values are given so as to help understand the invention.

The present inventors have found that a thermosensitive gel based on low molecular weight methyl cellulose is highly biocompatible and biodegradable and can be used for sustained release of a parenteral drug. The present invention has been achieved based on this finding.

The present invention will now be described in detail.

In one aspect, the present invention is directed to a ubiquitous injectable thermosensitive gel for drug delivery including a low molecular weight natural polymer alone without a salting-out salt.

More specifically, the present invention is directed to a thermosensitive gel for parenteral drug delivery composed of thermoreversible methyl cellulose alone wherein the thermoreversible methyl cellulose has a molecular weight of 10 to 20 kDa.

As used herein, the term "thermosensitive gel" means a drug delivery carrier that undergoes a phase change with varying temperatures.

The natural polymer used in the gel for drug delivery according to the present invention has a block copolymer structure consisting of a hydrophobic region with a high degree of substitution and a hydrophilic region with a low degree of substitution or where no substitution takes place. Due to this structure, a thermoreversible physical gel is formed in an aqueous solution. The hydrophobic region locally stabilizes the water structure and destroys the water structure upon heating to enhance its hydrophobic interaction, resulting in gelation.

The natural polymer is biodegradable in vivo. Particularly, the biodegradability of the natural polymer increases as the molecular weight of the natural polymer decreases.

The natural polymer used in the present invention is a thermoreversible polysaccharide, preferably methyl cellulose having a molecular weight of 10 to 20 kDa.

Methyl cellulose (MC) is a hydrophobically modified non-ionic cellulose derivative that forms a thermoreversible physical gel in an aqueous solution. Methyl cellulose is a heterogeneous alternating block copolymer structure consisting of a hydrophobic region with a high degree of substitution and a hydrophilic region with a low degree of substitution or where no substitution takes place (see Kundu, K. K, Polymer. 42 (2001) 2015-2020). As explained previously, the hydrophobic region destroys water structure upon heating to enhance its hydrophobic interaction, causing gelation. Commercial MC with a degree of substitution (DS) of 1.4 to 2.0 undergoes a sol-gel transition upon heating at a concentration of 1.0 to 2.5% in water.

For application of methyl cellulose (MC) to in situ-forming drug delivery systems that are gelled at body temperature, the reverse (negative) thermal gelation mechanism of MC generally needs to be modified with a polymer, a non-electrolyte or an additive, such as a salt.

When it is intended to gel MC at body temperature (~37° C.), it is common to reduce the gelation temperature (≥55° C.) of MC by the use of MC at an increased concentration or the addition of a salt. However, the use of MC at an increased concentration increases the viscosity of the solution, making the solution difficult to handle. The addition of an excess of a salting-out salt, such as ammonium sulfate or sodium triphosphate, causes cytotoxicity.

The present inventors have found that the gelation temperature of methyl cellulose whose molecular weight is greatly reduced to 10 to 20 kDa by enzymatic treatment can be lowered to body temperature in the range of 35 to 40° C.

Figure 1:
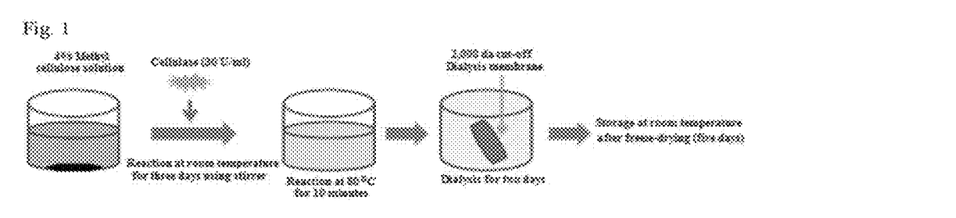
FIG. 1 is a schematic diagram showing a procedure for preparing low molecular weight methyl cellulose according to the present invention.

For example, the methyl cellulose having a low molecular weight of 10 to 20 kDa may be obtained by treatment with an enzyme, such as cellulase. A more detailed procedure for preparing the low molecular weight methyl cellulose is shown in FIG. 1.

Herein, the methyl cellulose with a molecular weight of 10 to 20 kDa is also expressed as "low molecular weight methyl cellulose." Methyl cellulose derivatives that do not lose their thermosensitivity are also included within the scope of the low molecular weight methyl cellulose.

The hydrogel for drug delivery according to the present invention may be produced using the low molecular weight methyl cellulose. The use of the low molecular weight methyl cellulose not only improves the biocompatibility of the hydrogel but also ensures slow in vivo degradation and release of the hydrogel, achieving in vivo release of the hydrogel.

The gel composed of the low molecular weight methyl cellulose is slowly degraded in vivo into lower molecular weight substances that are harmless to humans and per se are released in vivo. Accordingly, there is no need for a separate procedure, such as a surgical operation, to remove the gel after drug release over a predetermined time period. The lower molecular weight substances are released in vivo mainly through the kidneys. This can be confirmed in Example 4 that follows.

The thermosensitive gel of the present invention can be effectively used in a sustained release drug delivery system and is particularly effective for the delivery of hydrophilic drugs.

When the low molecular weight methyl cellulose with high biodegradability is mixed with a hydrophilic drug, such as a hydrophilic peptide/protein drug, an aqueous copolymer solution is prepared at a temperature lower than the gelation temperature of the methyl cellulose and can thus be used as a drug delivery liquid in which the drug is partially or completely dissolved.

Particularly, the low molecular weight methyl cellulose can be gelled in vivo even without the addition of any salt and is thus highly biocompatible and biodegradable.

Examples of drug substances that can be included in the gel of the present invention include proteins, polypeptides, carbohydrates, inorganic materials, antibiotics, antineoplastic agents, local anesthetics, antiangiogenic agents, vasoactive agents, anticoagulants, immunomodulators, cytotoxic agents, antiviral agents, antibodies, neurotransmitters, psychoactive drugs, oligonucleotides, lipids, cells, tissues, tissue or cell aggregates, and combinations thereof. Other drug substances include cancer chemotherapeutic agents, such as cytokines, chemokines, lymphokines, and substantially purified nucleic acids, and vaccines, such as attenuated influenza virus. Substantially purified nucleic acids that can be incorporated include genomic nucleic acid sequences, cDNAs encoding proteins, expression vectors, antisense molecules that bind to complementary nucleic acid sequences to inhibit transcription or translation, and ribozymes.

The kind of drugs usable in the gel of the present invention is not fundamentally limited but a hydrophilic drug, a protein drug or a nucleic acid-based drug is particularly preferred.

The thermosensitive gel of the present invention may also include at least one drug or therapeutic agent for a short-term therapeutic effect or treatment. The drug or therapeutic agent may be added to the natural polymer used to make the gel prior to, during, or after the dissolution of the polymer in solution. Preferably, the drug or therapeutic agent is added prior to the dissolution of the polymer in solution to facilitate a more uniform dispersion or dissolution of the drug or therapeutic agent.

A variety of techniques are known by which the drug or therapeutic agent can be incorporated into the gel (polymer), including, but not limited to, spray drying, solvent evaporation, phase separation, rapid freezing, and solvent extraction.

The drug or therapeutic agent is included in the gel from about 0.1 to about 100% by weight, preferably from about 1 to about 50% by weight, more preferably from about 10 to about 30% by weight, based on the weight of the gel. The drug or therapeutic agent may also be present in an amount of 0.01 to 95% by weight, based on the weight of the gel. The amount or concentration of the drug or therapeutic agent included in the gel will depend on the absorption, inactivation, and excretion rates of the drug or therapeutic agent as well as the delivery rate of the polymer in the gel.

The thermosensitive gel for drug delivery according to the present invention is in a liquid phase at room temperature. Immediately after injection into a subject, the liquid gel becomes a gel due to body temperature. The drug or therapeutic agent contained in the thermosensitive gel will diffuse into the extracellular matrix of the subject and will be released to the targeted site in a controlled manner.

In a further aspect, the present invention is directed to a method for preparing the low molecular weight methyl cellulose and a method for producing the thermosensitive gel using the low molecular weight methyl cellulose.

The thermosensitive gel can be produced using standard technique known to one skilled in art. The techniques, amounts, temperature, and time required to produce the thermosensitive gel for drug delivery according to the present invention will be known to those of ordinary skill of the art, as described in Example 1 that follows.

The gel of the present invention may optionally further include a small amount of a salting-out salt but is preferably produced using the low molecular weight methyl cellulose alone.

The sensitivity of the gel to various temperatures, e.g., the ability of the gel to reversible transition from a liquid at room temperature to a gel at body temperature, can be determined using standard assays or techniques that measure viscosity and volume change at various temperatures, using, for example, a viscometer.

In another aspect, the present invention includes a pharmaceutical composition for controlled drug release including the biodegradable and biocompatible gel and a plurality of drugs or therapeutic agents contained therein.

The present invention also includes a method for treating a disease, disorder or condition which includes introducing the composition into a patient in need of a drug or therapeutic agent and a method for producing the system. The drug or therapeutic is the same as that described above.

That is, the present invention is directed to a pharmaceutical composition for sustained release of a drug, including the thermosensitive gel including the thermoreversible methyl cellulose having a molecular weight of 10 to 20 kDa and a desired drug, and the use of the pharmaceutical composition.

The thermosensitive gel of the present invention can be prepared into bioabsorbable, biodegradable, and biocompatible preparations. The term "bioabsorbable" means that the polymer is capable of disappearing from its initial application site in the body, with or without degradation of the dispersed polymer molecules. The term "biodegradable" means that the polymer is capable of breaking down or degrading within the body, by hydrolysis or enzymatic degradation. The term "biocompatible" means that all of the components are nontoxic in the body.

The therapeutic agent or drug delivery system of the present invention may be suitably injected or otherwise delivered (e.g., by implanting, placing into a body cavity or potential space, coating a tissue surface of the body or coating the surface of an implantable device) to humans or other mammals suffering from a disease state or condition against which the drug(s) included in the drug delivery system are therapeutically effective. Particularly, the composition is preferably delivered parenterally. The term "parenteral" includes intramuscular, intraperitoneal, intraabdominal, subcutaneous, intravenous or intraarterial.

The composition of the present invention can be typically formulated into an injectable preparation.

The thermosensitive gel can be used as an injectable drug delivery carrier or as a functional support for tissue regeneration. To this end, the thermosensitive gel is required to have low viscosity and should be formed rapidly. In addition, the thermosensitive gel is required to have low molecular weight for its easy release from the body. The use of the low molecular weight methyl cellulose makes the thermosensitive gel biocompatible, has low viscosity and maintains the low molecular weight.

The injectable composition of the present invention may be injected or implanted into the body of a human or other mammal in any suitable manner, and preferably by injection through a hypodermic needle.

For example, the composition of the present invention may be administered by injection or other means intraarticularly, intravascularly, into the urogenital tract, subcutaneously, intramuscularly, intradermally, intracranially, intrapericardially, intrapleurally, or into any body cavity or potential space. Alternately, the composition may be introduced via a catheter or a syringe to a joint such as during an arthroscopic procedure, or into the urogenital tract, into the vasculature, into the pericardial or pleural space, or into any body cavity or potential space within the body, during operative, surgical, diagnostic or interventional procedures. The composition can be administrated to a confined area or tissue to achieve a higher local concentration of the drug, forming a sustained release depot. In other applications, topical application of the composition to an open surgical or traumatic wound, to a burn, or to the skin or other tissue surface may be carried out.

Particularly, the composition of the present invention slowly releases the drug in vivo when injected into a target site in the body.

The thermosensitive gel of the present invention is suitable for use as a sustained or controlled release matrix for the drug. When the gel matrix is coupled with one or more therapeutic agents contained intimately therein, a biodegradable sustained release delivery system is provided.

The term "sustained release" (i.e., extended release or controlled release) is used herein to refer to a drug delivery system or composition that is introduced into the body of a human or other mammal, or that is applied to an open wound, burn or tissue surface or into a body cavity or potential body space, and that continuously releases a stream of one or more therapeutic agents over a predetermined time period and at a therapeutic level sufficient to achieve a desired therapeutic effect throughout the predetermined time period.

In the Examples section that follows, the composition of the present invention was confirmed to provide sustained release of the drug over a period of about 20 days to 40 days.

As explained earlier, the hydrogel of the present invention is degraded into substances harmless to humans after the lapse of a predetermined period time and the substances are then released in vivo through the kidneys. Therefore, when the composition of the present invention is injected into a target site in the body via a general syringe or catheter, the drug is slowly released and is maintained at a constant concentration in the circulating blood for a long time, achieving its excellent pharmacological effects and avoiding the need for a separate procedure, such as a surgical operation, to remove the drug delivery carrier.

According to the sustained release drug delivery system of the present invention, a drug or therapeutic agent can be released in a controlled manner to a targeted site in a subject.

In one embodiment, the thermosensitive gel is utilized to provide site-specific release of a drug or therapeutic agent to a subject. In another embodiment, the thermosensitive gel includes at least one drug or therapeutic agent that can be administered to a subject, so that the drug or therapeutic agent is released by diffusion from and/or degradation of the gel.

It is to be noted that dosage values of the composition will also vary with the type and severity of a disease, disorder, or condition being treated. It is to be further understood that for any particular subject, specific dosage regimens should be adjusted over time according to the individual need and the professional judgment of the person administering or supervising the administration of the composition. In vivo dosages may be based on in vitro release studies in cell culture or on in vivo animal models.

The method and composition of the present invention provide optimal delivery of a drug or therapeutic agent, because it releases the drug or therapeutic agent in a controlled manner. The result of controlled delivery is that the drug is delivered over a desired period of time. A slower and steadier rate of delivery may in turn result in a reduction in the frequency with which the drug or therapeutic agent must be administered to an animal.

The rate of release of a drug or therapeutic agent depends on many factors, particularly the rate of degradation of the biodegradable polymer of the gel. Yet another factor that affects the release rate of a drug or therapeutic agent is the particle size of the drug or therapeutic agent. By adjusting the factors discussed above, degradation, diffusion, and controlled release may be varied over very wide ranges. For example, release may be designed to occur over hours, days, or months.

As described above, the thermosensitive gel for parenteral drug delivery using the low molecular weight methyl cellulose according to the present invention has high biocompatibility and biodegradability, is suitable for use in a long-term sustained release preparation, and is very useful as a drug delivery carrier because it increases the pharmacological effects and stability of a drug.

MODE FOR CARRYING OUT THE INVENTION

The present invention will be explained in detail with reference to the following embodiments and accompanying drawings. These embodiments are provided for illustrative purposes only and are not meant in any way to limit the scope of the invention. Other embodiments that can be easily inferred from the following embodiments by those skilled in the art are also intended to come within the scope of the appended claims.

Example 1: Preparation of Low Molecular Weight Methyl Cellulose

The molecular weight of methyl cellulose (MC, Mn=14, 000, viscosity=15 cps) was reduced by cellulase treatment. Then, methyl cellulose having a specific molecular weight was separated using a 2,000 Da cut-off dialysis membrane, followed by freeze-drying.

The procedure for the preparation of the low molecular weight methyl cellulose is schematically shown in FIG. 1.

Figure 2:
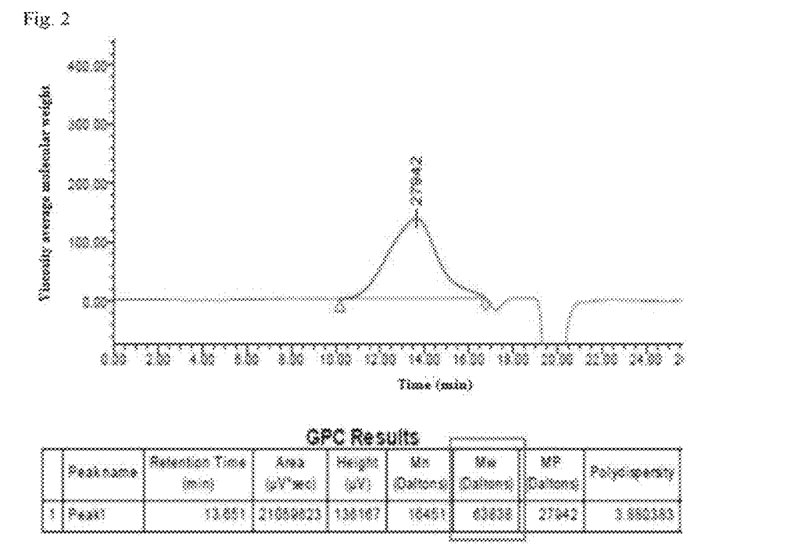
FIG. 2 shows the results of GPC analysis for the molecular weight of methyl cellulose before treatment with cellulase as an enzyme.
Figure 3:
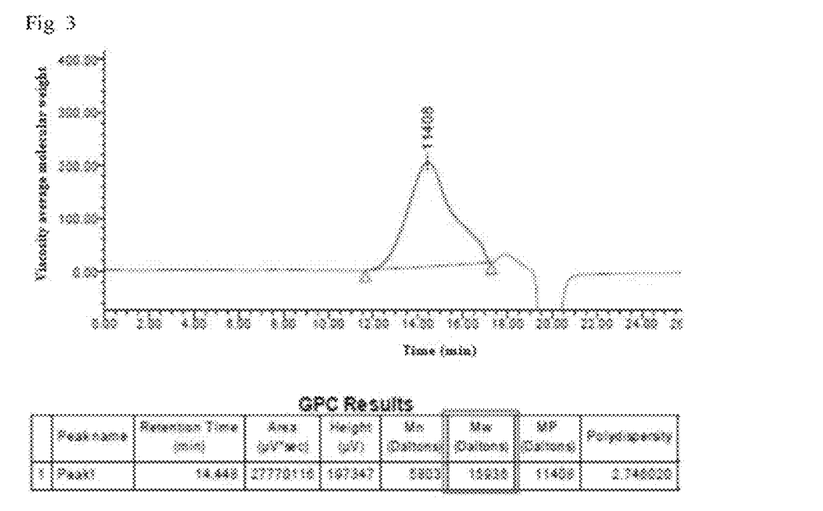
FIG. 3 shows the results of GPC analysis for the molecular weight of methyl cellulose prepared after treatment with cellulase as an enzyme.

The molecular weights of the methyl cellulose before the cellulase treatment and the low molecular weight methyl cellulose prepared by the cellulase treatment were determined by gel permeation chromatography (GPC) and are shown in FIGS. 2 and 3, respectively.

As can be seen from these figures, the molecular weight of the methyl cellulose before the enzymatic treatment was about 64 kDa and that of the low molecular weight methyl cellulose prepared by the enzymatic treatment was about 15 kDa, which corresponded to almost one-fourth of the original molecular weight.

Example 2: Characterization of Low Molecular Weight Methyl Cellulose Hydrogel

A thermosensitive hydrogel was produced using the low molecular weight methyl cellulose alone without the addition of any salting-out salt and its characteristics were analyzed.

The gel was produced in accordance with a method known in the art. Specifically, 20 wt % of the low molecular weight methyl cellulose prepared in Example 1 was sufficiently mixed with distilled water, and then the mixture was homogenized using a stirrer at a low temperature (4° C.). The low-temperature homogenization was performed, considering that the low molecular weight methyl cellulose is not dissolved at high temperature on account of its characteristics. After stirring for about 1 h, the mixture was stored at low temperature before use for subsequent experiments.

(1) Gelation Temperature

Figure 4:
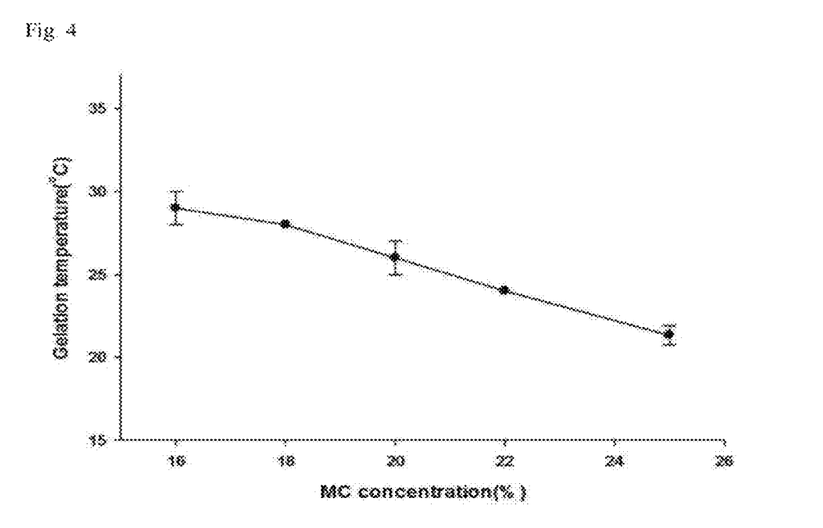
FIG. 4 is a graph showing the gelation temperatures of low molecular weight methyl cellulose used in the present invention at different concentrations.

First, the gelation temperatures of the low molecular weight methyl cellulose were measured at different concentrations by the tube inverting method. The results are shown in FIG. 4. The gelation temperature decreased with increasing concentration of the methyl cellulose, confirming that a thermosensitive hydrogel could be produced using the low molecular weight methyl cellulose alone without the addition of a salting-out salt.

(2) Viscosity

Figure 5:
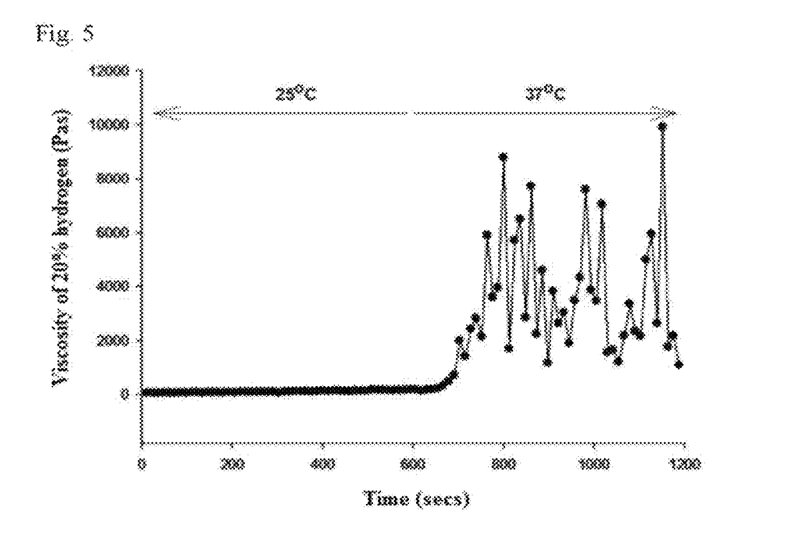
FIG. 5 is a graph showing the viscosities of a 20% hydrogel according to the present invention at different temperatures.

The viscosities of the 20% hydrogel at different temperatures were measured using a rheometer. The results are shown in FIG. 5.

The hydrogel was maintained in a solution state without any change in viscosity at room temperature. The hydrogel was converted to a gel with increased viscosity when the temperature was increased to body temperature.

(3) Cytotoxicity Analysis

3T3-L1 cells were grown on a transwell plate. The low molecular weight methyl cellulose hydrogel produced in Example 1 was placed into the inserts of the transwell plate and its cytotoxicity was observed.

Figure 6:
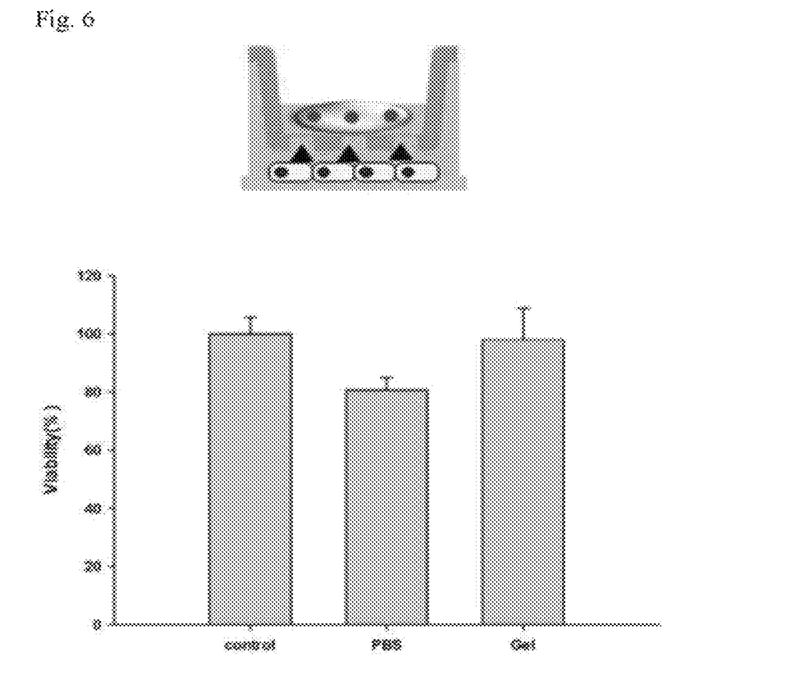
FIG. 6 shows a schematic diagram showing an experiment to confirm the cytotoxicity of a thermosensitive gel according to the present invention and the results of the experiment.

FIG. 6 shows a schematic diagram showing the cytotoxicity experiment and the experimental results. The low molecular weight methyl cellulose hydrogel was found to have no toxicity.

Comparative Example 1: Cytotoxicity of Various Salting-Out Salts

Figure 7:
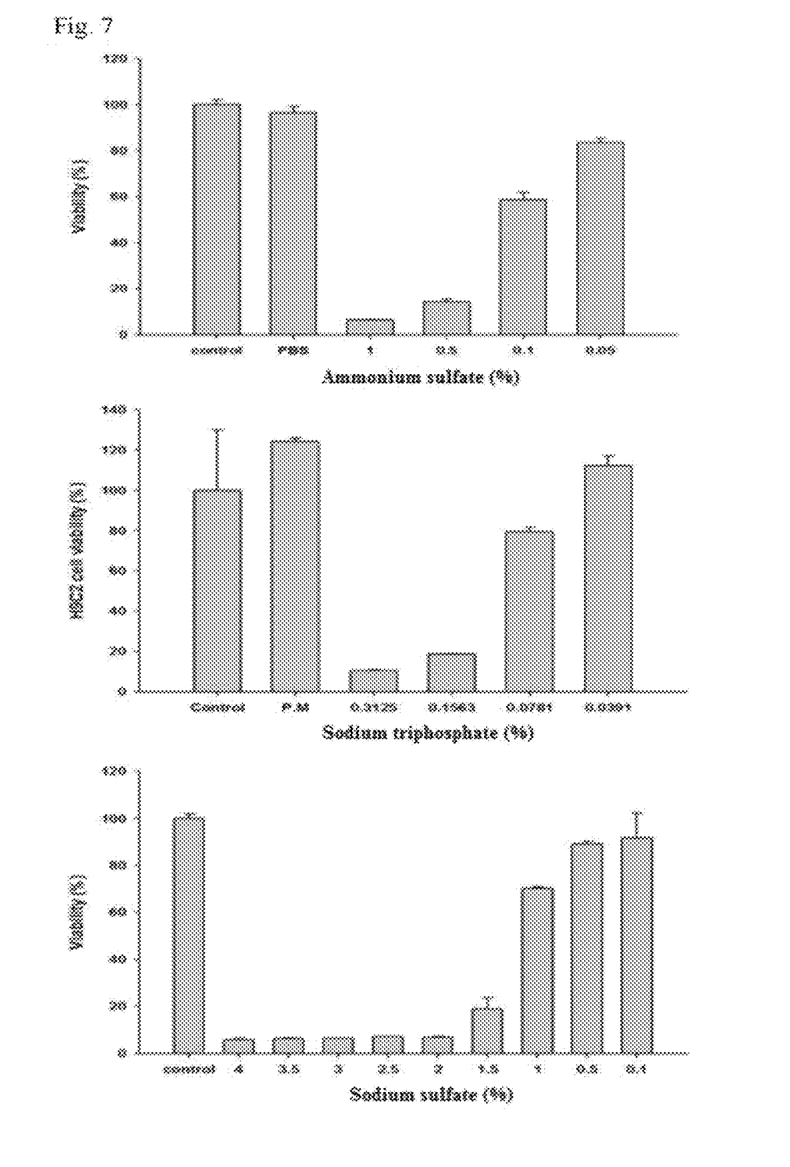
FIG. 7 graphically shows the toxicities of ammonium sulfate (AS), sodium triphosphate (STPP), and sodium sulfate (SS) as salting-out salts.

The toxicities of ammonium sulfate (AS), sodium triphosphate (STPP), and sodium sulfate (SS) as salting-out salts in H9C2 cells were analyzed to compare with the non-toxicity of the low molecular weight methyl cellulose. The results are shown in FIG. 7.

The salting-out salts were confirmed to cause toxicities even at low concentrations in the cells.

Example 3: Drug Release Efficacy of the Low Molecular Weight Methyl Cellulose Gel (In Vitro Release Test)

In this example, the ability of the hydrogel to release drugs was confirmed. First, each of BSA and FGF21 as protein drugs and exenatide as a peptide drug was loaded into the hydrogel produced in Example 1 and drug release testing was conducted.

Each drug-loaded hydrogel was solidified in a microtube. Then, phosphate buffer saline (PBS) was placed on the gel and the drug was allowed to release at 37° C. and 100 rpm.

Figure 8:
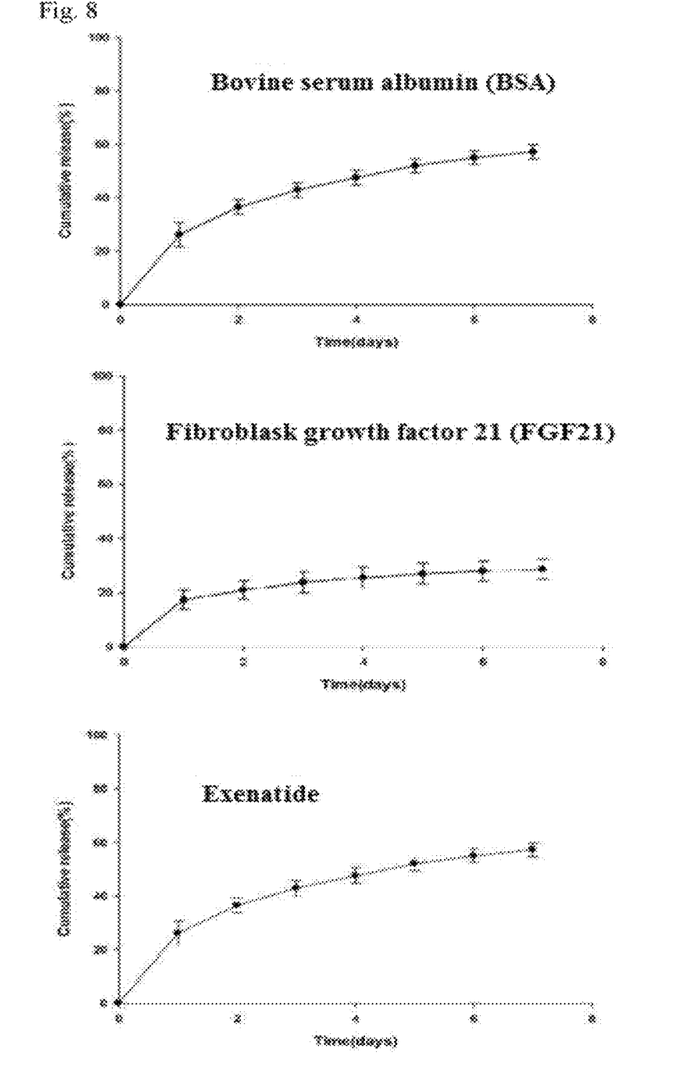
FIG. 8 shows the ability of a hydrogel according to the present invention to release proteins (BSA and FGF21) and a peptide (exenatide).

As a result, the protein and the peptide drugs were slowly released from the hydrogel, as shown in FIG. 8.

Figure 9:
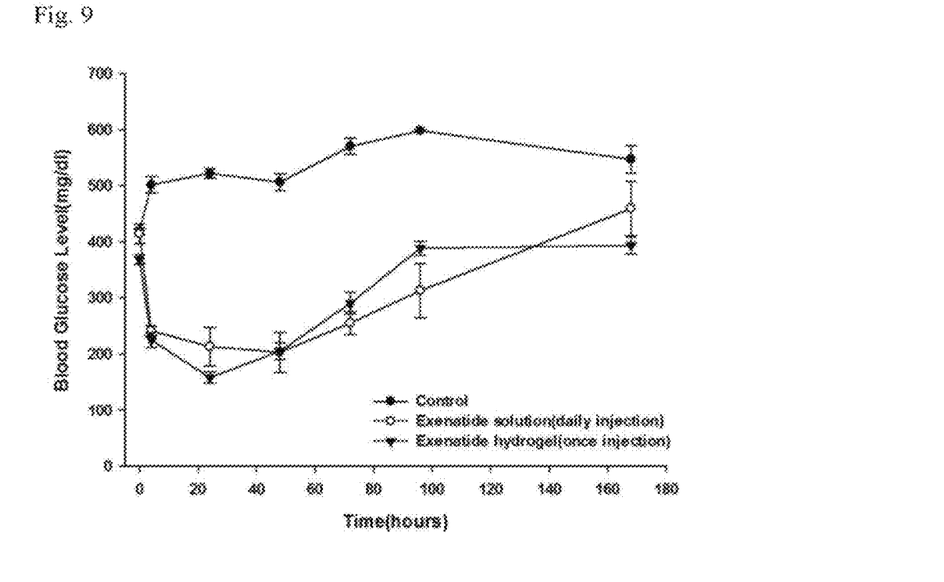
FIG. 9 is a graph showing the effect of an exenatide-containing hydrogel in a type 1 diabetes animal model.

Example 4: Animal Experiments of the Low Molecular Weight Methyl Cellulose Gel 4-1. Type 1 Diabetes Animal Models Streptozotocin was administered to mice to establish type 1 diabetes models. Exenatide was loaded into the hydrogel to obtain an exenatide preparation and exenatide was dissolved in phosphate buffer saline (PBS) to obtain another exenatide preparation. The exenatide hydrogel was administered once by injection and the exenatide solution was administered daily for 5 days. After administration, changes in the blood glucose level of the models were observed for a predetermined period of time. The results are shown in FIG. 9.

Exenatide should be injected daily to regulate the blood glucose level due its very short half life. In contrast, the exenatide hydrogel released exenatide for one week even when administered in a single dosage, and as a result, the blood glucose level was regulated.

4-2. Type 2 Diabetes Animal Models

First, mice were continuously given high-fat diets to induce obesity. The blood glucose levels of the obese mice were measured.

Thereafter, FGF21 was loaded into the hydrogel to obtain an FGF21 preparation and FGF21 was dissolved in PBS to obtain another FGF21 preparation. The FGF21 hydrogel was administered twice a week and the FGF21 solution was divided into two groups, one of which was administered daily and the other was administered twice a week. The groups were observed for blood glucose level.

Figure 10:
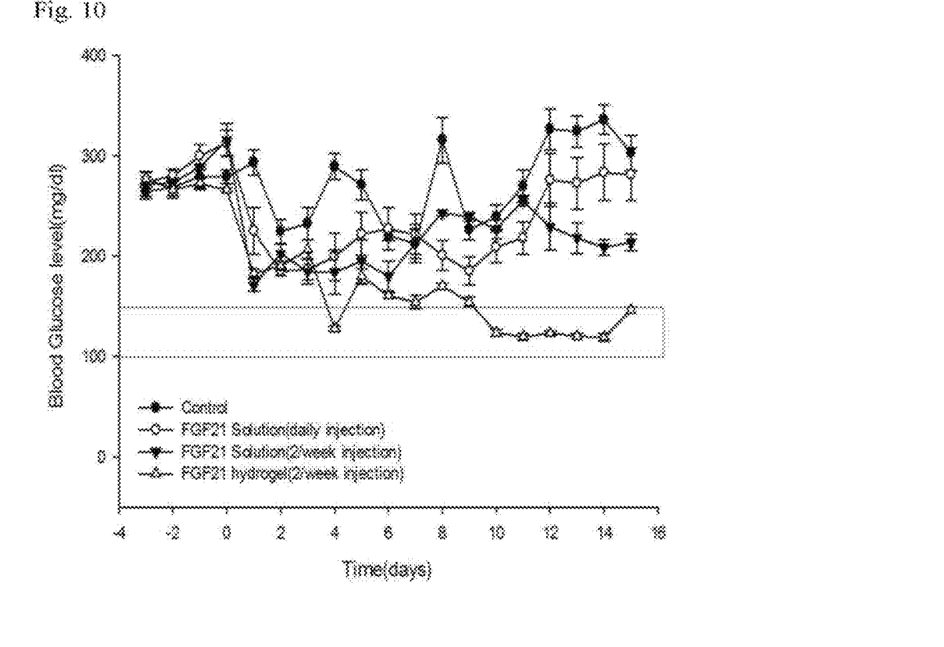
FIG. 10 is a graph showing the effect of an FGF21-containing hydrogel in a type 2 diabetes animal model.

The results are shown in FIG. 10. 2 weeks after administration, the FGF21 hydrogel reduced the blood glucose level to the normal range.

4-3. Confirmation of In Vivo Release Performance of the Hydrogel

To confirm the in vivo release performance of the hydrogel, Cy5.5 as a fluorescent dye was conjugated to methyl cellulose and gels were produced in the same manner as in Example 1. Thereafter, each gel was injected subcutaneously into a mouse and the release of the gel was observed over a predetermined period of time.

Figure 11:
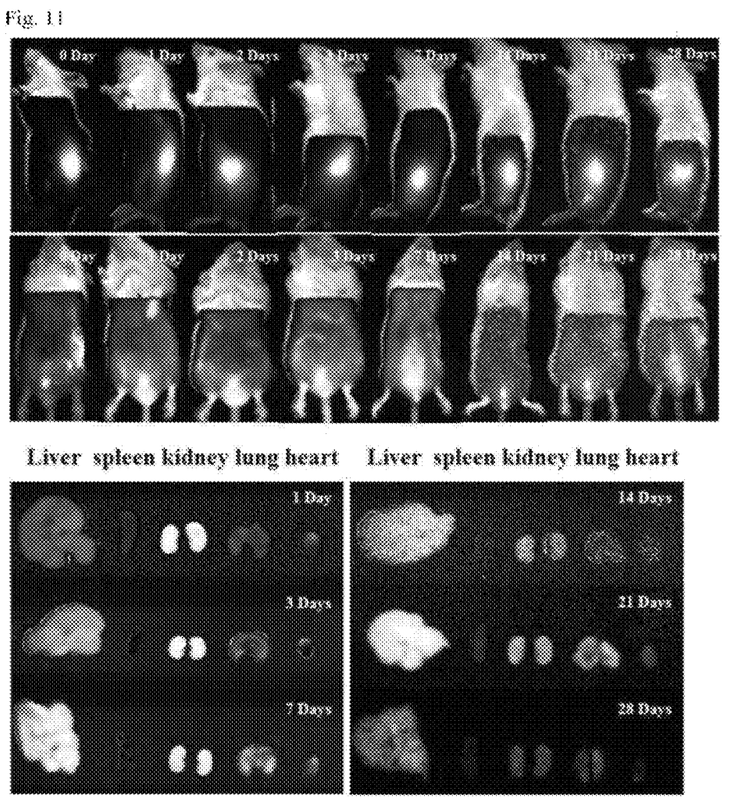
FIG. 11 shows images confirming the elimination efficiency of hydrogel in vivo.

As a result, the injected gel was slowly spread in the mouse with the lapse of time and was released in vivo mainly through the kidneys, as shown in FIG. 11.

These results can lead to the conclusion that the hydrogel of the present invention is slowly degraded in vivo into lower molecular weight substances that are harmless to humans and per se are released in vivo. Therefore, there is no need for a separate procedure, such as a surgical operation, to remove the gel after drug release over a predetermined time period.

INDUSTRIAL APPLICABILITY

As is evident from the foregoing, the parenteral drug delivery system of the present invention is based on low molecular weight methyl cellulose alone as a natural polymer and is thus free from toxicity problems encountered in the use of salting-out salts in conventional parenteral drug delivery systems, ensuring high biocompatibility and biodegradability. Particularly, the low molecular weight methyl cellulose is gelled at body temperature to slowly release a drug in vivo and it per se is slowly degraded in vivo into lower molecular weight substances harmless to humans, which are then released in vivo. Therefore, there is no need for a separate surgical operation to remove the gel after release of the drug over a predetermined time period. In addition, since a single dosage of the parenteral drug delivery system is sufficient to maintain the pharmacological effects of the drug, the need for frequent administration of the parenteral drug delivery system can be avoided, ensuring improved convenience for patients. The formed gel is maintained for a long period of time and thus exhibits many outstanding effects, such as release of the drug over a desired period of time. Therefore, the gel is very useful as a drug delivery carrier.

The invention claimed is:

1. A sustained release composition suitable for parenteral drug delivery consisting of a thermosensitive gel and one or more of FGF21 or exenatide, and optionally a drug that is one or more of a hydrophilic drug, a protein drug, or a nucleic acid based drug, wherein the thermosensitive gel consists of methyl cellulose having a molecular weight of 10 to 20 kDa and optionally water, and the sustained release composition is optionally in the form of an injectable preparation.

2. The sustained release composition according to claim 1, wherein the methyl cellulose has an average molecular weight of 15 kDa.

3. The sustained release composition according to claim 1, wherein the gel is formed at a body temperature in the range of 35 to 40° C.

4. The sustained release composition according to claim 1, wherein the drug is a hydrophilic drug.

5. The sustained release composition according to claim 1, which is in the form of an injectable preparation.

6. The sustained release composition according to claim 5, wherein the parenteral delivery is intramuscular, intraperitoneal, intraabdominal, subcutaneous, intravenous or intraarterial.

7. A method for preparing the methyl cellulose having a molecular weight of 10 to 20 kDa used in a thermosensitive gel, the method comprising treating methyl cellulose having a molecular weight of 50 to 70 kDa with cellulase and dialyzing the enzymatically treated methyl cellulose using a dialysis membrane.

8. The sustained release composition according to claim 1, wherein the drug is a protein drug.

9. The sustained release composition according to claim 1, wherein the drug is a nucleic acid-based drug.

* * * * *